United States Patent [19]

Gaylord, Jr. et al.

[11] Patent Number: 4,987,891
[45] Date of Patent: Jan. 29, 1991

[54] EMERGENCY CERVICAL COLLAR

[75] Inventors: John F. Gaylord, Jr., Matthews; Susan L. Dean, Charlotte, both of N.C.

[73] Assignee: Medical Specialties, Inc., Charlotte, N.C.

[21] Appl. No.: 292,416

[22] Filed: Dec. 30, 1988

[51] Int. Cl.⁵ .............................................. A61F 5/04
[52] U.S. Cl. ........................... 128/87 B; 128/DIG. 23
[58] Field of Search ..................... 128/75, 76 R, 87 B, 128/89 R, DIG. 15, DIG. 23, 87 R

[56] References Cited

U.S. PATENT DOCUMENTS

| | | | |
|---|---|---|---|
| 3,042,026 | 7/1962 | Monfardini | 128/75 |
| 3,374,785 | 3/1968 | Gaylord, Jr. | 128/75 |
| 3,530,853 | 9/1970 | Bond | 128/75 |
| 3,696,810 | 10/1972 | Gaylord, Jr. | 128/75 |
| 3,756,226 | 9/1973 | Calabrese et al. | 128/75 |
| 3,810,466 | 5/1974 | Rogers | 128/75 |
| 3,850,164 | 11/1974 | Hare | 128/75 |
| 3,964,474 | 6/1976 | Fox | 128/87 B |
| 4,043,325 | 8/1977 | Ochs et al. | 128/75 |
| 4,205,667 | 6/1980 | Gaylord, Jr. | 128/75 |
| 4,232,663 | 11/1980 | Newton | 128/75 |
| 4,413,619 | 11/1983 | Garth | 128/76 R |
| 4,422,454 | 12/1983 | English | 128/870 |
| 4,702,233 | 10/1987 | Omicioli | 128/75 |
| 4,708,129 | 11/1987 | Pujals, Jr. | 128/75 |
| 4,712,540 | 12/1987 | Tucker et al. | 128/76 R |
| 4,718,412 | 1/1988 | Nesbitt | 128/87 R |

Primary Examiner—Robert A. Hafer
Assistant Examiner—Charles H. Sam
Attorney, Agent, or Firm—Bell, Seltzer, Park & Gibson

[57] ABSTRACT

This invention is directed to a low cost cervical collar for use in emergency situations when there is a possible cervical/spinal injury. The cervical collar comprises a flexible foam plastic body member having sufficient length to substantially encircle the neck of the wearer in use. The body member includes a medial portion and opposite wing portions arranged to overlie the ears and provide substantial support for the head. The cervical collar is also provided with a hole centered at the front thereof to provide access to the throat in the event an emergency tracheotomy is needed. In a preferred embodiment, the cervical collar further includes a solid plastic sheet overlying a substantial portion of the body to provide additional strength and support.

9 Claims, 1 Drawing Sheet

U.S. Patent    Jan. 29, 1991    Sheet 1 of 1    4,987,891
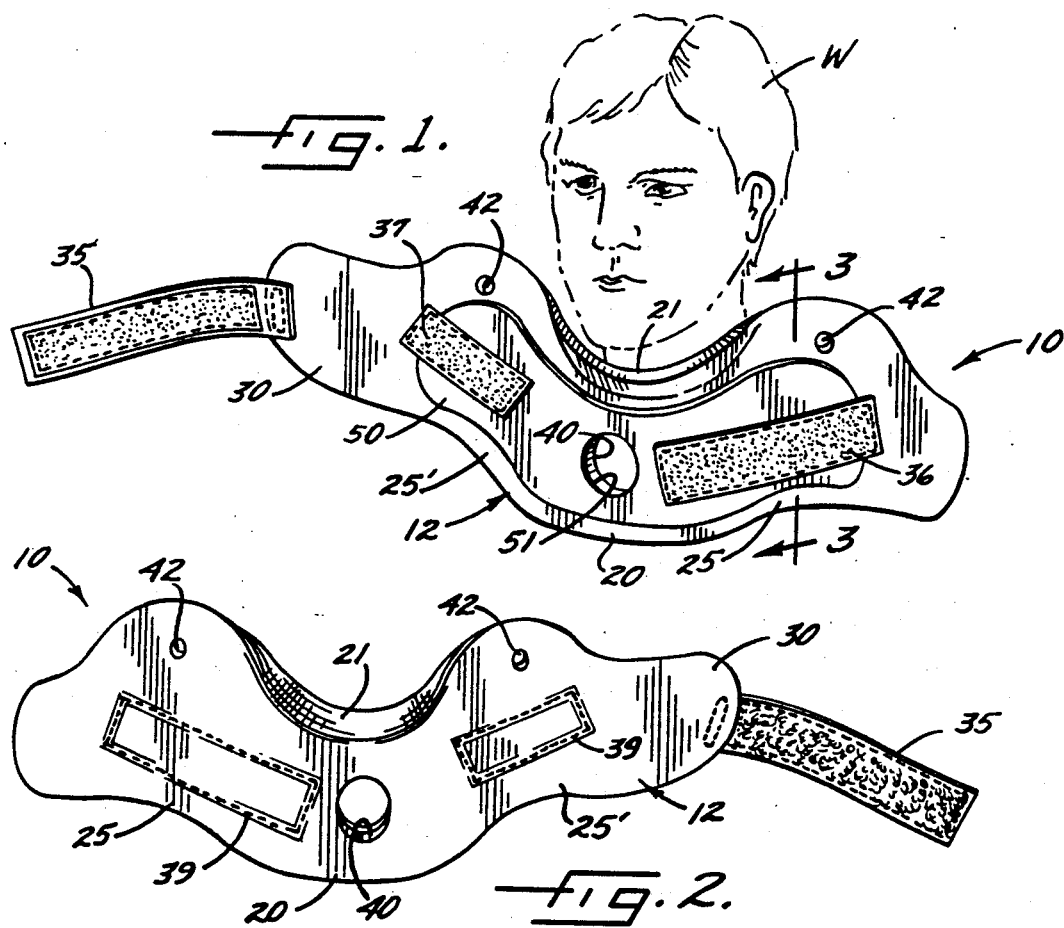
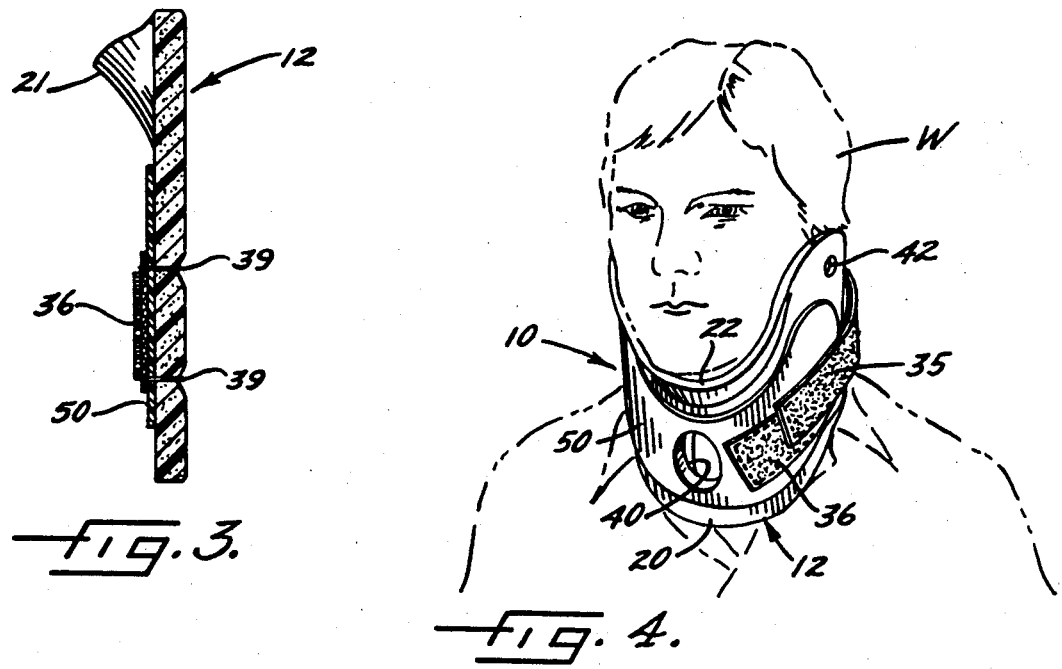

EMERGENCY CERVICAL COLLAR

FIELD OF THE INVENTION

This invention relates to cervical collars, particularly to cervical collars for providing support for the head and neck of an injured person and adapted to avoid further injury to the person during the administration of prehospital care.

BACKGROUND OF THE INVENTION

During the administration of emergency prehospital care, it is conventional to use a cervical collar where there is a possible cervical/spinal injury. Cervical collars of various designs are well known in the medical field, including commonly owned U.S. Pat. Nos. 3,374,785, 3,696,810 and 4,205,667. Previously, if the patient bled on the collar, which commonly happens in emergency situations, the collar would be cleaned for subsequent uses with no harmful consequences. Now, contact with blood and other bodily fluids includes the risk of getting contagious diseases so it may be hazardous to reuse a cervical collar that has been bled on. There are methods of sterilizing medical equipment, such as with a water/bleach solution, but it is generally preferred to dispose of the equipment once it has been used. However, current designs for cervical collars are excessively expensive for budget conscious emergency health care providers.

For example, a basic design for a cervical collar is disclosed in U.S. Pat. No. 3,850,164 to Hare. The collar is a one piece elongate design with end portions having an increased width that fit up against the side of the user's head below the ear to provide additional positioning and support for the user's head. The cervical collar is made of high density foam with a knit fabric cover. However, this type of cervical collar, while it is simpler than most, is more suited for use by a patient during the recovery from an injury or medical ailment. The high density foam provides comfortable support due to its softness and flexibility, however such foam is rather expensive. Further, the foam must be of substantial thickness to provide the necessary support for the wearer's head. Finally, the fabric cover adds substantially to the cost of the collar.

Accordingly, it is an object of the present invention to provide a low cost, effective design for a cervical collar, which is suitable for one time use.

It is also an object of the present invention to provide an emergency cervical collar that provides improved stability to the head and neck of an injured person at low cost.

It is a further object of the present invention to provide an emergency cervical collar which avoids the disadvantages and drawbacks and prior art as discussed above.

SUMMARY OF THE INVENTION

The above and other objects of the present invention are achieved by the provision of a cervical collar comprising a generally flat, unitary body member having sufficient longitudinal length and flexibility to permit the same to encircle the wearer's neck in use. The body member is composed of a foam plastic material of substantially uniform thickness throughout and comprises a medial portion and opposite wing portions. The medial portion is adapted to extend between the chin and the sternum of the wearer in use and to have an upper edge portion which is inclined outwardly from the plane of the remainder of the body member to define a chin engaging support. The wing portions have a sufficient lateral width so as to be adapted to overlie the ears of the wearer in use and thereby provide substantial lateral stability to the head of the wearer. The cervical collar also includes fastening means mounted to the body member for releasably securing the body member in encircling relation about the neck of the wearer.

In the preferred embodiment, the collar also includes a one-piece, relatively thin, solid plastic sheet attached to the body member and overlying at least a substantial portion of the medial portion and each of the wing portions. The plastic sheet provides additional resilience and strength to the collar.

BRIEF DESCRIPTION OF THE DRAWINGS

Some of the features and advantages of the invention have been stated and other will become apparent as the description proceeds when taken in conjunction with the accompanying drawings, in which:

FIG. 1 is a front perspective view of the cervical collar as it is aligned to encircle the wearer's neck;

FIG. 2 is a rear perspective view of the cervical collar;

FIG. 3 is a sectional view of the cervical collar taken along the line 3—3 in FIG. 1; and FIG. 4 is a perspective view of the cervical collar in use encircling the wearer's neck.

DETAILED DESCRIPTION OF THE PREFERRED EMBODIMENT

Referring more particularly to the drawings, FIGS. 1 through 4 illustrate a preferred embodiment of the cervical collar generally indicated by the numeral 10. The cervical collar 10 comprises a flexible foam plastic body member 12 having an extensive longitudinal length sufficient to substantially encircle the neck of a wearer. The body member 12 further has a lateral width which is approximately one eighth to one quarter of the length of the collar. The body member 12 also has a thickness, best illustrated in FIG. 3, which is very small relative to either the length or width of the body member, therefore giving the body member 12 a long and flat appearance. The collar, while it is flexible to permit the body member 12 to encircle the wearer's neck as shown in FIG. 4 also has sufficient resilience to resist bending and provide support for the wearer's head and neck.

The body member 12 is made of a foam plastic material such as cross-linked polyethylene foam having a density of approximately 5 lbs/cu.ft. In the preferred embodiment, it is between about ¼ to ½ inches thick.

The elongate body member 12 more specifically comprises a medial portion 20 generally centrally disposed therein. The medial portion 20 is adapted to extend between the chin and the sternum of the wearer in use and to have an upper edge portion 21 which is inclined outwardly from the plane of the remainder of the body member. The upper edge portion 21 thereby defines a chin engaging support to support the chin of the wearer and the incline eliminates an otherwise rough edge against the chin. On the opposite ends of the medial portion 20 along the elongate body member are a pair of wing portions 25, 25'. The wing portions 25, 25' also have sufficient lateral width to be adapted to overlie the ears of the wearer in use and thereby provide substantial lateral stability to the head of the wearer. It should be apparent from the drawings that the medial portion is disposed in a particular manner relative to the wing portions to fit the physiological shape of the body of the wearer. More particularly, the lower edge of the medial portion 20 is offset downwardly relative to the wing portions 25, 25'. This permits the medial portion to extend below the level of the shoulder and rest solidly against the sternum to provide substantial support for the chin. Similarly, the wing portions 25, 25' rest on the shoulders and extend far above the level of the chin to essentially cradle the head. The wing portions 25, 25', particularly the portions overlying the ears, tend to also prevent the wearer's head from turning axially about the neck. Thus, with the collar properly positioned, the head and neck of the wearer are provided with firm support against movement in both lateral directions as well as in the forward and rear plane.

The wing portion 25' includes an outer end portion 30 which is adapted to overlie the back of the neck of the wearer in use. The outer end portion 30 has a lateral width which is less than the lateral width of the remainder of the wing portion 25'.

The collar is held in position by fastening means such as fastening straps 35 and 36. The straps are comprised of a longitudinally extending flexible first strap 35 fixed to and extending outwardly from one end of the wing portion 25', and a second strap 36 fixed to the outer surface of the opposite wing portion 25. The straps 35, 36 have outer surfaces which mount mating "Velcro" type fastening means, with the rear surface of the strap 35 mounting loop type fastening means and the outer surface of the strap 36 mounting hook type fastening means in the illustrated embodiment. Thus the fastening means releasably secure the body member in an encircling relation about the neck of the wearer. The second strap 36 entirely overlies the body member 12. The fastening straps are preferably sewn onto the body member by stitching 39, however other conventional means of attachment may be suitable. A further strap 37 is also attached by stitching 39 to the outer surface of the wing portion 25', and which is of similar construction to that of the strap 36. The function of the strap 37 is set forth below.

The preferred embodiment of the cervical collar also features an opening 40 extending through the medial portion of the body member to provide access to the wearer's throat for an emergency tracheotomy. Such access may be very important since neck injuries are often accompanied by other injuries that may block the airway. With the opening 40, an emergency tracheotomy may be performed with the cervical collar in place and supporting the head and neck of the injured person. As a further convenience, openings 42 are positioned in the wing portions to overlie the ears of the wearer to facilitate hearing. In some emergency situations, paramedics talk to the injured person to keep him aroused and alert. The openings 42 therefore facilitate such communication.

To provide further strength and resilience for the collar 10, a relatively thin, low density solid plastic sheet 50 is attached to the outer surface of the body member 12 such that it overlies at least a substantial portion of the medial portion 20 and each of the wing portions 25, 25'. The sheet 50 is preferably attached to the body member by the stitching 39 of the fastening straps 36 and 37. More particularly, the second fastening strap 36 and the additional fastening strap 37 entirely overlie the body member 12 and at least a substantial portion of the plastic sheet 50 such that the stitching 39 extends through the plastic sheet 50 and the body member 12. The stitching 39 therefore also serves to secure the plastic sheet to the body. The plastic sheet 50 may be alternatively attached by adhesive or other means. The sheet 50 is further provided with an opening 51 in alignment with the opening 40 to provide access to the throat of the patient as discussed above. It should be noted that the sheet 50 provides additional strength for the cervical collar, allowing the opening 40 to be formed in the medial portion 20 of the body member 12.

In FIG. 4, the collar 10 is shown in position encircling the neck of the wearer and it is held in place by the fastening means 35 and 36. The use of the described "Velcro" type fastening means permits the collar to be positioned and secured very quickly and easily, and if the collar should need adjusting, the fastening straps provide virtually an infinite array of adjustments. The fastening straps 36 and 37 are also placed and arranged for cooperation with the components of an emergency extrication device for removing an injured person from an automobile or other confined locations. An emergency extrication device of the described type is disclosed in commonly owned U.S. Pat. No. 4,422,454.

The foregoing description is to be considered illustrative rather than restrictive of the invention, and those modifications which come within the meaning and range of equivalence of the claims are to be included therein.

That which I claim is:

1. A low cost cervical collar adapted to encircle a wearer's neck to support the head and neck against movement in both lateral directions as well as in the forward and rear plane, and comprising a generally flat, unitary body member having a sufficient longitudinal length and flexibility to permit the same to substantially encircle the wearer's neck in use, said body member being composed of a foam plastic material of substantially uniform thickness throughout and comprising a medical portion and opposite wing portions, with said medial portion adapted to extend between the chin and sternum of the wearer in use and having an upper edge portion which is inclined outwardly from the plane of the remainder of the body member to define a chin engaging support, and with said wing portions each having a sufficient lateral width so as to be adapted to overlie the ears with the wearer in use and thereby provide substantial lateral stability to the head of the wearer, at least one of said wing portions further comprising an outer end portion having a lateral width less than that of the remainder of said one wing portion, and with said end portion being adapted to overlie the back of the neck of the wearer in use, a one-piece, relatively thin, solid plastic sheet attached to said body member and overlying at least a substantial portion of said medial portion and each of said wing portions, and such that said plastic sheet provides additional resilience and strength to the cervical collar, and fastening means mounted to said body member for releasably securing said body member in encircling relation about the neck of the wearer, said fastening means comprising a longitudinally extending flexible strap fixed to the outer end of one of said wing portions, and a second strap fixed to the opposite wing portion, and wherein one of said first and second straps mounts hook type releasable attachment means and the other of said first and second straps mounts mating loop type releasable attachment means, and wherein the entire second strap overlies said body member and at least a portion the other of said first and second straps mounts mating loop type releasable attachment means, and wherein the entire second strap overlies said body member and at least a portion of said plastic sheet, and with said second strap being secured to said plastic sheet and said body member by stitching which extends through said plastic sheet and said body member, and such that said stitching also serves to secure said plastic sheet to said body member.

2. The cervical collar as defined in claim 1 wherein said foam plastic of said body member has a density of about 5 lbs/cu.ft., and said body member has a thickness of between about ¼ and 178 inches.

3. The cervical collar as defined in claim 1 wherein each of said wing portions includes a relatively small opening therethrough, with said openings being positioned to overlie the ears of the wearer to thereby facilitate hearing.

4. The cervical collar as defined in claim 11 wherein said one of said wing portions having said first strap fixed thereto further comprises an outer end portion having a lateral width less than that of the remainder of said one wing portion, and with said end portion being adapted to overlie the back of the neck of the wearer in use.

5. The cervical collar as defined in claim 1 further comprising an opening extending through said medial portion of said body member and said plastic sheet to provide access to the wearer's throat for an emergency tracheotomy.

6. The cervical collar as defined in claim 1 further comprising an additional strap entirely overlying said body member and at least a portion of the plastic sheet on the side of said opening opposite said second strap, and with said additional strap being secured to said plastic sheet and said body member by stitching which extends through said plastic sheet and said body member, and such that said stitching also serves to secure said plastic sheet to said body member.

7. The cervical collar as defined in claim 6 wherein said additional strap includes at least one of said hook type releasable attachment means and said loop type releasable attachment means.

8. A low cost cervical collar adapted to encircle a wearer's neck to support the head and neck against movement in both lateral directions as well as in the forward and rear plane, and comprising a generally flat, unitary body member having a sufficient longitudinal length and flexibility to permit the same to substantially encircle the wearer's neck in use, said body member being composed of a foam plastic material of substantially uniform thickness throughout and comprising a medial portion and opposite wing portions, with said medial portion adapted to extend between the chin and sternum of the wearer in use and having an upper edge portion which is inclined outwardly from the plane of the remainder of the body member to define a chin engaging support, and with said wing portions each having a sufficient lateral width so as to be adapted to overlie the ears of the wearer in use and thereby provide substantial lateral stability to the head of the wearer, a one piece, relatively thin, solid plastic sheet attached to said body member and overlying at least a substantial portion of said medial portion and each of said wing portions, and such that said plastic sheet provides additional resilience and strength to the cervical collar, fastening means mounted to said body member for releasably securing said body member in encircling relation about the neck of the wearer, wherein said fastening means comprises a longitudinally extending flexible first strap fixed to the outer end of one of said wing portions, and a second strap fixed to the opposite wing portion, and wherein one of said first and second straps mounts hook type releasable attachment means and the other of said first and second straps mounts mating loop type releasable attachment means, and wherein the entire second strap overlies said body member and at least a portion of said plastic sheet, and with said second strap being secured to said plastic sheet and said body member by stitching which extends through said plastic sheet and said body member, and such that said stitching also serves to secure said plastic sheet to said body member.

9. A low cost cervical collar adapted to encircle a wearer's neck to support the head and neck against movement in both lateral directions as well as in the forward and rear plane, and comprising a generally flat, unitary body member having a sufficient longitudinal length and flexibility to permit the same to substantially encircle the wearer's neck in use, said body member being composed of a foam plastic material of substantially uniform thickness throughout and comprising a medial portion and opposite wing portions, with said medial portion adapted to extend between the chin and sternum of the wearer in use and having an upper edge portion which is inclined outwardly from the plane of the remainder of the body member to define a chin engaging support, and with said wing portions each having a sufficient lateral width so as to be adapted to overlie the ears of the wearer in use and thereby provide substantial lateral stability to the head of the wearer, a one piece, relatively thin, solid plastic sheet attached to said body member and overlying at least a substantial portion of said medial portion and each of said wing portions, and such that said plastic sheet provides additional resilience and strength to the cervical collar, and fastening means mounted to said body member for releasably securing said body member in encircling relation about the neck of the wearer, wherein said fastening means comprises a longitudinally extending flexible first strap fixed to the outer end of one of said wing portions, and a second strap fixed to the opposite wing portion, and wherein one of said first and second straps mounts hook type releasable attachment means and the other of said first and second straps mounts mating loop type releasable attachment means, and an additional strap entirely overlying said body member and at least a portion of the plastic sheet on the side of said opening opposite said second strap, and with said additional strap being secured to said plastic sheet and said body member by stitching which extends through said plastic sheet and said body member, and such that said stitching also serves to secure said plastic sheet to said body member.

* * * * *

UNITED STATES PATENT AND TRADEMARK OFFICE
CERTIFICATE OF CORRECTION

PATENT NO. : 4,987,891

DATED : January 29, 1991

INVENTOR(S) : John F. Gaylord, Jr. et al.

It is certified that error appears in the above-identified patent and that said Letters Patent is hereby corrected as shown below:

Column 4, line 48, "with" should be -- of --.

Column 5, lines 6-9, please delete "the other of said first and second straps mounts mating loop type releasable attachment means, and wherein the entire second strap overlies said body member and at least a portion".

Column 5, line 18, "178" should be -- 1/2 --.

Column 5, line 24, "Claim 11" should be -- Claim 8 --.

Signed and Sealed this

Twenty-ninth Day of June, 1993

Attest:

MICHAEL K. KIRK

Attesting Officer

Acting Commissioner of Patents and Trademarks